United States Patent
Osborne et al.

(10) Patent No.: US 12,144,802 B2
(45) Date of Patent: Nov. 19, 2024

(54) PHARMACEUTICAL COMPOSITIONS OF ROFLUMILAST AND SOLVENTS CAPABLE OF DISSOLVING HIGH AMOUNTS OF THE DRUG

(71) Applicant: ARCUTIS BIOTHERAPEUTICS, INC., Westlake Village, CA (US)

(72) Inventors: David W. Osborne, Fort Collins, CO (US); Babak N. Tofig, Westlake Village, CA (US); Frank Watanabe, Westlake Village, CA (US)

(73) Assignee: ARCUTIS BIOTHERAPEUTICS, INC., Westlake Village, CA (US)

( * ) Notice: Subject to any disclaimer, the term of this patent is extended or adjusted under 35 U.S.C. 154(b) by 0 days.

(21) Appl. No.: 18/217,287

(22) Filed: Jun. 30, 2023

(65) Prior Publication Data
US 2024/0108609 A1    Apr. 4, 2024

Related U.S. Application Data

(60) Provisional application No. 63/406,921, filed on Sep. 15, 2022.

(51) Int. Cl.
| | | |
|---|---|---|
| *A61K 31/44* | (2006.01) | |
| *A61K 9/00* | (2006.01) | |
| *A61K 9/14* | (2006.01) | |
| *A61K 47/10* | (2017.01) | |
| *A61K 47/14* | (2017.01) | |
| *A61K 47/22* | (2006.01) | |

(52) U.S. Cl.
CPC ............ *A61K 31/44* (2013.01); *A61K 9/0014* (2013.01); *A61K 47/10* (2013.01); *A61K 47/14* (2013.01); *A61K 47/22* (2013.01)

(58) Field of Classification Search
CPC ........ A61K 47/14; A61K 31/44; A61K 47/10; A61K 47/22
See application file for complete search history.

(56) References Cited

U.S. PATENT DOCUMENTS

| | | |
|---|---|---|
| 4,482,537 A | 11/1984 | El-Menshawy et al. |
| 5,374,661 A | 12/1994 | Betlach |
| 5,712,298 A | 1/1998 | Amschler |
| 5,863,560 A | 1/1999 | Osborne |
| 6,056,955 A | 5/2000 | Fischetti et al. |
| 6,060,085 A | 5/2000 | Osborne |
| 6,106,848 A | 8/2000 | Preuilh et al. |
| 6,117,915 A | 9/2000 | Pereira et al. |
| 6,214,322 B1 | 4/2001 | Castro et al. |
| 7,470,791 B2 | 12/2008 | Kohl et al. |
| 7,951,398 B2 | 5/2011 | Dietrich et al. |
| 8,293,288 B2 | 10/2012 | Ma |
| 8,338,648 B2 | 12/2012 | Stock et al. |
| 8,377,663 B2 | 2/2013 | Lintner et al. |
| 8,536,206 B2 | 9/2013 | Kohl et al. |
| 8,618,142 B2 | 12/2013 | Kohl et al. |
| 8,884,034 B2 | 11/2014 | Daynard et al. |
| 9,205,044 B2 | 12/2015 | Linder |
| 9,649,302 B2 | 5/2017 | Vakkalanka |
| 9,884,050 B1 | 2/2018 | Osborne |
| 9,895,359 B1 * | 2/2018 | Osborne ................ A61K 9/145 |
| 9,907,788 B1 | 3/2018 | Osborne |
| 10,105,354 B1 | 10/2018 | Osborne |
| 10,172,841 B2 | 1/2019 | Osborne |
| 10,940,142 B2 | 3/2021 | Osborne |
| 11,129,818 B2 | 9/2021 | Osborne et al. |
| 11,707,454 B2 | 7/2023 | Berk et al. |
| 11,793,796 B2 | 10/2023 | Osborne |
| 2005/0112162 A1 | 5/2005 | Drader |
| 2005/0244339 A1 | 11/2005 | Jauernig et al. |
| 2006/0084684 A1 | 4/2006 | Bolle et al. |
| 2006/0110415 A1 | 5/2006 | Gupta |
| 2006/0153905 A1 | 7/2006 | Carrara |
| 2006/0204452 A1 | 9/2006 | Lathrop et al. |
| 2006/0204526 A1 | 9/2006 | Lathrop |
| 2006/0234006 A1 | 10/2006 | Tenra |
| 2007/0048241 A1 | 3/2007 | Obukowho et al. |
| 2007/0098660 A1 | 5/2007 | Taneri et al. |

(Continued)

FOREIGN PATENT DOCUMENTS

| | | |
|---|---|---|
| CN | 1655782 A | 8/2005 |
| CN | 101061993 A | 10/2007 |

(Continued)

OTHER PUBLICATIONS

Ataman ("1,3 butylene glycol" (published Oct. 15, 2019) retrieved on Feb. 21, 2024, available from https://www.atamanchemicals.com/1-3-butylene-glycol_u27932/)(Year 2019) (Year: 2019).*
International Search Report and Written Opinion mailed Oct. 25, 2023 in corresponding PCT Application No. PCT/US2023/026794 (12 pages).
Ali, et al., "Skin pH: From Basic Science to Basic Skin Care," Acta Derm. Venereal., vol. 93, pp. 261-267 (1-9), Tbl. SI (2013).
Assawasuwannakit, et al., "Quantification of the Forgiveness of Drugs to Imperfect Adherence," CPT Pharmacometrics Syst. Pharmacol., vol. 4, e4, pp. 204-211 (2015).
Ayala-Bravo HA, Quintanar-Guerrero D, Naik A, Kalia YN, Cornejo-Bravo JM, Ganem-Quintanar A., "Effects of sucrose oleate and sucrose laureate on in vivo human stratum corneum permeability," Pharm Res., 2003;20(8):1267-73.

(Continued)

*Primary Examiner* — John S Kenyon
*Assistant Examiner* — Rehana Ismail
(74) *Attorney, Agent, or Firm* — Rothwell, Figg, Ernst & Manbeck, P.C.

(57) ABSTRACT

Topical pharmaceutical compositions comprising roflumilast and solvents that are capable of dissolving high amounts of roflumilast. The pharmaceutical compositions are capable of dissolving high amounts of roflumilast relative to other commonly used solvents in approved topical pharmaceutical compositions. The solvents are particularly useful when combined with water to maintain high levels of dissolved roflumilast, which is highly insoluble in water.

20 Claims, No Drawings

(56) References Cited

U.S. PATENT DOCUMENTS

| | | |
|---|---|---|
| 2007/0207107 A1 | 9/2007 | Winckle et al. |
| 2007/0258935 A1 | 11/2007 | McEntire et al. |
| 2007/0259009 A1 | 11/2007 | Linder |
| 2007/0287689 A1 | 12/2007 | Harada |
| 2008/0200005 A1 | 1/2008 | Chang et al. |
| 2008/0039405 A1 | 2/2008 | Langley |
| 2008/0045572 A1 | 2/2008 | Linder |
| 2008/0280958 A1 | 11/2008 | Bolle et al. |
| 2009/0104132 A1 | 4/2009 | Segura-Orsoni |
| 2009/0214628 A1 | 8/2009 | Rijk |
| 2009/0220583 A1 | 9/2009 | Pereswetoff-Morath et al. |
| 2011/0117182 A1 | 5/2011 | Ahluwalia et al. |
| 2011/0212157 A1 | 9/2011 | Edelson et al. |
| 2012/0252793 A1 | 10/2012 | Bream et al. |
| 2013/0005816 A1 | 1/2013 | Chen |
| 2013/0017282 A1 | 1/2013 | Ma |
| 2013/0018104 A1 | 1/2013 | Lathrop et al. |
| 2013/0217742 A1 | 8/2013 | Yang |
| 2014/0112991 A1 | 4/2014 | Johnson et al. |
| 2014/0275184 A1 | 9/2014 | Jones et al. |
| 2014/0275265 A1 | 9/2014 | Mattison |
| 2014/0296191 A1 | 10/2014 | Patel et al. |
| 2014/0303215 A1 | 10/2014 | Bolle et al. |
| 2015/0099752 A9 | 4/2015 | Bernal Anchuela et al. |
| 2015/0297601 A1 | 10/2015 | Henkin |
| 2016/0030435 A1 | 2/2016 | Henkin |
| 2017/0152273 A1 | 6/2017 | Merchant |
| 2017/0266289 A1 | 9/2017 | Lipari |
| 2018/0353490 A1 | 12/2018 | Osborne |
| 2019/0015398 A1 | 1/2019 | Osborne |
| 2019/0091333 A1 | 3/2019 | Osborne |
| 2019/0175491 A1 | 6/2019 | Abraham et al. |
| 2019/0365642 A1 | 12/2019 | Osborne |
| 2020/0155524 A1 | 5/2020 | Welgus et al. |
| 2020/0163944 A1 | 5/2020 | Osborne et al. |
| 2021/0161870 A1 | 6/2021 | Welgus et al. |
| 2021/0275509 A1 | 9/2021 | Welgus et al. |
| 2021/0386719 A1 | 12/2021 | Osborne et al. |
| 2022/0175743 A1 | 6/2022 | Berk et al. |
| 2022/0211730 A1 | 7/2022 | Osborne et al. |
| 2023/0091358 A1 | 3/2023 | Osborne |
| 2023/0134782 A1 | 5/2023 | Osborne et al. |
| 2023/0201177 A1 | 6/2023 | Osborne |
| 2023/0285319 A1 | 9/2023 | Osborne et al. |
| 2023/0310346 A1 | 10/2023 | Osborne et al. |
| 2023/0310397 A1 | 10/2023 | Osborne et al. |
| 2023/0321057 A1 | 10/2023 | Berk et al. |
| 2023/0338275 A1 | 10/2023 | Osborne |

FOREIGN PATENT DOCUMENTS

| | | |
|---|---|---|
| CN | 101854907 A | 10/2010 |
| CN | 108992673 B | 11/2020 |
| CN | 112384199 A | 2/2021 |
| EP | 1511516 A1 | 3/2005 |
| EP | 1 906 916 A2 | 4/2008 |
| JP | 2005529930 A | 10/2005 |
| JP | 2007119432 A | 5/2007 |
| JP | 2007533606 A | 11/2007 |
| JP | 2009034537 A | 2/2009 |
| JP | 2011219364 A | 11/2011 |
| JP | 2012532871 A | 12/2012 |
| WO | WO 9501338 A1 | 1/1995 |
| WO | WO 9810768 A1 | 3/1998 |
| WO | WO 03099278 A1 | 12/2003 |
| WO | WO 2003099334 A1 | 12/2003 |
| WO | WO 2005016296 A1 | 2/2005 |
| WO | WO 2005115322 A1 | 12/2005 |
| WO | WO 2013030789 A1 | 3/2013 |
| WO | WO 2013081565 A1 | 6/2013 |
| WO | WO 2014055801 A1 | 4/2014 |
| WO | WO 2014130922 A1 | 8/2014 |
| WO | WO 2014201541 A1 | 12/2014 |
| WO | WO 2015132708 A1 | 9/2015 |
| WO | WO 2016033308 A1 | 3/2016 |
| WO | WO 2017216738 A1 | 12/2017 |
| WO | WO 2018144093 A2 | 8/2018 |
| WO | WO 2018226584 A1 | 12/2018 |
| WO | WO 2019060379 A1 | 3/2019 |
| WO | WO 2021045804 A1 | 3/2021 |
| WO | 2021/155173 A1 | 8/2021 |

OTHER PUBLICATIONS

Barakat NS., "Evaluation of glycofurol-based gel as a new vehicle for topical application of naproxen," AAPS PharmSciTech., 2010;11(3):1138-46.

Benson HA., "Transdermal drug delivery: penetration enhancement techniques," Curr Drug Deliv., 2005;2(1):23-33.

Berkó S, et al., Monitoring of skin penetration and absorption with a new in vivo experimental model,: Farmacia, 2014;62(6):1157-63.

Bialik W, Walkers KA, Brain KR, Hadgraft J. Some factors affecting the in vitro penetration of ibuprofen through human skin. Int J Pharm. 1993;92:219-23.

Bjorklund S, et al., "The effects of polar excipients transcutol and dexpanthenol on molecular mobility, permeability, and electrical impedance of the skin barrier," J Colloid Interface Sci., 2016;479:207-20.

Bonina FP, Montenegro L., "Effects of some non-toxic penetration enhancers on in vitro heparin skin permeation from gel vehicles," Int J Pharm., 1994;111(2):191-6.

Cazares-Delgadillo J, Naik A, Kalia YN, Quintanar-Guerrero D, Ganem-Quintanar A., "Skin permeation enhancement by sucrose esters: a pH-dependent phenomenon," Int J Pharm. 2005;297(1-2):204-212.

Chadha G, Sathigari S, Parsons DL, Jayachandra Babu R., "In vitro percutaneous absorption of genistein from topical gels through human skin," Drug Dev Ind Pharm., 2011;37(5):498-505.

Chang RK, Raw A, Lionberger R, Yu L., "Generic development of topical dermatologic products: formulation development, process development, and testing of topical dermatologic products," AAPS J., 2013;15(1):41-52.

Cho YA, Gwak HS., "Transdermal delivery of ketorolac tromethamine: effects of vehicles and penetration enhancers." Drug Dev Ind Pharm., 2004;30(6):557-64.

Choi JS, Cho YA, Chun IK, Jung SY, Gwak HS., "Formulation and evaluation of ketorolac transdermal systems," Drug Deliv., 2007;14(2):69-74.

Csizmazia E, Erös G, Berkesi O, Berkó S, Szabó-Révész P, Csányi E., "Penetration enhancer effect of sucrose laurate and Transcutol on ibuprofen," J Drug Deliv Sci Technol., 2011;21(5):411-415.

Dugard PH, Walker M, Mawdsley SJ, Scott RC., "Absorption of some glycol ethers through human skin in vitro," Environ Health Perspect., 1984;57:193-7.

Fabin B, Touitou E., "Localization of lipophilic molecules penetrating rat skin in vivo by quantitative autoradiography," Int J Pharm. 1991;74(1):59-65.

FDA, Inactive Ingredient Guide (Jan. 1996).

Feldman, et al., "Psoriasis: Improving Adherence to Topical Therapy," J. Am. Acad. Dermatol., vol. 59, pp. 1009-1016 (2008).

Gad SC, Cassidy CD, Aubert N, Spainhour B, Robbe H., "Nonclinical vehicle use in studies by multiple routes in multiple species," Int J Toxicol., 2006;25(6):499-521.

Ganem-Quintanar A, Lafforgue C, Falson-Rieg F, Buri P., "Evaluation of the transepidermal permeation of diethylene glycol monoethyl ether and skin water loss," Int J Pharm. 1997;147(2):165-71.

Gao, et al., "Sunscreen Formulas with Multilayer Lamella Structure," Cosmetics & Toiletries, vol. 118, pp. 41-52 (Oct. 2003).

Godwin DA, Kim NH, Felton LA., "Influence of Transcutol CG on the skin accumulation and transdermal permeation of ultraviolet absorbers," Eur J Pharm Biopharm., 2002;53(1):23-7.

Gungor S, Bergisadi N., "Effect of penetration enhancers on in vitro percutaneous penetration of nimesulide through rat skin," Pharmazie., 2004;59(1):39-41.

Gwak H, Chun I., "Effect of vehicles and penetration enhancers on the in vitro percutaneous absorption of tenoxicam through hairless mouse skin," Int J Pharm., 2002;236(1-2):57-64.

(56) References Cited

OTHER PUBLICATIONS

Gwak HS, Kim SU, Chun IK, "Effect of vehicles and enhancers on the in vitro permeation of melatonin through hairless mouse skin," Arch Pharm Res., 2002;25(3):392-6.

Gwak HS, Oh IS, Chun IK., "Transdermal delivery of ondansetron hydrochloride: effects of vehicles and penetration enhancers," Drug Dev Ind Pharm. 2004;30(2):187-94.

Harrison JE, Watkinson AC, Green DM, Hadgraft J, Brain K., "The relative effect of azone and Transcutol on permeant diffusivity and solubility in human stratum corneum," Pharm Res. 1996;13(4):542-6.

Helton DR, Osborne DW, Pierson SK, Buonarati MH, Bethem RA., "Pharmacokinetic profiles in rats after intravenous, oral, or dermal administration of dapsone," Drug Metab Dispos., 2000;28(8):925-9.

Hirata K, Helal F, Hadgraft J, Lane ME., "Formulation of carbenoxolone for delivery to the skin," Int J Pharm., 2013;448(2):360-5.

Hirata K, Mohammed D, Hadgraft J, Lane ME., "Influence of lidocaine hydrochloride and penetration enhancers on the barrier function of human skin," Int J Pharm. 2014;477(1-2):416-20.

Javadzadeh Y, Hamishehkar H., "Enhancing percutaneous delivery of methotrexate using different types of surfactants," Colloids Surf B Biointerfaces, 2011;82(2):422-6.

Javadzadeh, et al., "Transcutol® (Diethylene Glycol Monoethyl Ether): A Potential Penetration Enhancer," Ch. 12, pp. 195-205, in N. Dragicevic, et al., eds., Percutaneous Penetration Enhancers Chemical Methods in Penetration Enhancement: Modification of The Stratum Corneum (2015).

Kim KH, Gwak HS., "Effects of vehicles on the percutaneous absorption of donepezil hydrochloride across the excised hairless mouse skin," Drug Dev Ind Pharm., 2011;37(9):1125-30.

Kircik, "Topical Treatment Adherence for Psoriasis," Skin Therapy Letter-Family Practice Edition, vol. 4, No. 2, pp. 4 & 5 (2008).

Koprda V, Bohacik L, & Hadgraft J, "Permeation of a Pyridoindol structure substance from the Transcutol/water/azone cosolvent system," In 5th International conference: Perspectives in Percutaneous Penetration, vol. 5B, pp. 163-164; 1997.

Labeling for DALIRESP® (roflumilast) Tablets (2013).

Labeling for ELOCON® (mometasone furoate) Cream (2013).

Leung, et al., "New Insights into Atopic Dermatitis," J. Clin. Invest., vol. 113, pp. 651-657 (2004).

Moghadam SH, Saliaj E, Wettig SD, Dong C, Ivanova MV, Huzil JT, et al., "Effect of chemical permeation enhancers on stratum corneum barrier lipid organizational structure and interferon alpha permeability," Mol Pharm., 2013;10(6):2248-60.

Mura P, Faucci MT, Bramanti G, Corti P., "Evaluation of transcutol as a clonazepam transdermal permeation enhancer from hydrophilic gel formulations," Eur J Pharm Sci., 2000;9(4):365-72.

O'Neil, et al., eds., The Merck Index, pp. 2822, 8379, 1536 (15th ed., 2013).

Osborne et al., "Skin Penetration and Permeation Properties of Transcutol®—Neat or Diluted Mixtures," AAPS PharmaSCITECH, vol. 19, No. 8, Nov. 2018, pp. 3512-3533.

Otto A, Wiechers JW, Kelly CL, Hadgraft J, du Plessis J, "Effect of penetration modifiers on the dermal and transdermal delivery of drugs and cosmetic active ingredients," Skin Pharmacol Physiol., 2008;21(6):326-34.

Panchagnula R, Ritschel WA., "Development and evaluation of an intracutaneous depot formulation of corticosteroids using Transcutol as a cosolvent: in-vitro, ex-vivo and in-vivo rat studies," J Pharm Pharmacol. 1991;43(9):609-14.

Physicians' Desk Reference, pp. 305, 748-52, 1432-35 (67th/2013 ed., 2012).

Puglia C, Bonina F, Trapani G, Franco M, Ricci M., "Evaluation of in vitro percutaneous absorption of lorazepam and clonazepam from hydro-alcoholic gel formulations," Int J Pharm. 2001;228(1-2):79-87.

Remane Y, Leopold CS, Maibach HI., "Percutaneous penetration of methyl nicotinate from ointments using the laser Doppler technique: bioequivalence and enhancer effects," J Pharmacokinet Pharmacodyn., 2006;33(6):719-35.

Rhee YS, Huh JY, Park CW, Nam TY, Yoon KR, Chi SC, et al., "Effects of vehicles and enhancers on transdermal delivery of clebopride." Arch Pharm Res., 2007;30(9):1155-61.

Ritschel WA, Barkhaus JK.. "Feasibility study for transdermal delivery of meperidine," Methods Find Exp Clin Pharmacol., 1988; 10(7):461-466.

Ritschel WA, Barkhaus JK., "Use of sorption promoters to increase systemic absorption of coumarin from transdermal drug delivery systems," Arzneimittelforschung, 1988;38(12):1774-7.

Ritschel WA, Hussain AS., "In vitro skin penetration of griseofulvin in rat and human skin from an ointment dosage form," Arzneimittelforschung, 1988;38(11):1630-2.

Ritschel WA, Panchagnula R, Stemmer K, Ashraf M., "Development of an intracutaneous depot for drugs: Binding, drug accumulation and retention studies, and mechanism of depot," Skin Pharmacol. 1991;4(4):235-45.

Rosenstock, "Understanding and Enhancing Patient Compliance with Diabetic Regimens," Diabetes Care, vol. 8, pp. 610-616 (1985).

Rougier A, Dupuis D, Lotte C Roguet R & H. Schaefer, "In vivo correlation between stratum corneum reservoir function and percutaneous absorption," J Invest Dermatol, 1983;81(275-278).

Salimi A, Hedayatipour N, Moghimipour E., "The effect of various vehicles on the naproxen permeability through rat skin: a mechanistic study by DSC and FT-IR techniques," Adv Pharm Bull., 2016;6(1):9-16.

Senyigit T, Padula C, Ozer O, Santi P., "Different approaches for improving skin accumulation of topical corticosteroids," Int J Pharm., 2009;380(1-2):155-60.

Shaaya AN, Kraus C, Bauman DH, Ritschel WA., "Pharmacokinetics and bioavailability of papaverine HCl after intravenous, intracorporeal and penis topical administration in beagle dogs," Methods Find Exp Clin Pharmacol., 1992; 14(5):373-8.

Study NCT01856764, "Topical Roflumilast in Adults with Atopic Dermatitis," sponsored by Takeda, available at https://clinicaltrials.gov/ (Jul. 2015).

Sullivan DW Jr, Gad SC, Julien M., "A review of the nonclinical safety of Transcutol(R), a highly purified form of diethylene glycol monoethyl ether (DEGEE) used as a pharmaceutical excipient," Food Chem Toxicol., 2014;72:40-50.

Sutton et al., "Characterization of a Liquid Crystal Stabilized Pharmaceutical Oil-in-Water Emulsion Optimized for Skin Delivery", Journal of Cosmetics, Dermatological Sciences and Applications, vol. 8, No. 4, Nov. 2018, pp. 207-217.

Tiossi RF, et al., "In vitro and in vivo evaluation of the delivery of topical formulations containing glycoalkaloids of Solanum lycocarpum fruits," Eur J Pharm Biopharm., 2014;88(1):28-33.

Touitou E, Levi-Schaffer F, Dayan N, Alhaique F, Riccieri F., "Modulation of caffeine skin delivery by carrier design: liposomes versus permeation enhancers." Int J Pharm., 1994;103(2):131-6.

Touitou E, Levi-Schaffer F, Shaco-Ezra N, Ben-Yossef R, Fabin B., "Enhanced permeation of theophylline through the skin and its effect on fibroblast proliferation," Int J Pharm. 1991; 70(1-2):159-66.

Urquhart, "The Electronic Medication Event Monitor: Lessons for Pharmacotherapy," Clin. Pharmacokinet., vol. 32, pp. 345-356 (1997).

V. Koprda et al., "Skin Penetration Studies of Transcutol Using Radiotracer Technique," GRC (1995), 10 pgs.

Watkinson AC, Hadgraft J, Bye A., "Aspects of the transdermal delivery of prostaglandins," Int J Pharm., 1991;74(2-3):229-36.

Yazdanian M, Chen E., "The effect of diethylene glycol monoethyl ether as a vehicle for topical delivery of ivermectin," Vet Res Commun., 1995;19(4):309-19.

Zaghloul, et al., "Objective Assessment of Compliance with Psoriasis Treatment," Arch. Dermatol., vol. 140, pp. 408-414 (2004).

Notification of Reasons for Rejection issued in JP2020-567541 dated Nov. 24, 2023, 9 pages.

Office Action issued in U.S. Appl. No. 18/453,674 dated Oct. 27, 2023 (13 pages).

Office Action issued in U.S. Appl. No. 17/155,679 dated Feb. 5, 2024 (9 pages).

(56) References Cited

OTHER PUBLICATIONS

Office Action issued in U.S. Appl. No. 18/345,692 dated Oct. 26, 2023 (68 pages).
Office Action issued in U.S. Appl. No. 18/345,732 dated Jan. 24, 2024 (12 pages).
Office Action issued in U.S. Appl. No. 18/345,760 dated Oct. 26, 2023 (19 pages).
Office Action issued in U.S. Appl. No. 18/353,870 dated Jan. 12, 2024 (10 pages).
Office Action issued in U.S. Appl. No. 18/353,869 dated Sep. 18, 2023 (7 pages).
Notification of Certification of Invalidity, Unenforceability, and/or Noninfringement for U.S. Pat. Nos. 9,884,050; 9,907,788; 10,940,142; 11,129,818; 11,793,796; and 11,819,496 Pursuant to § 505(j)(2)(B)(iv) of the Federal Food, Drug, & Cosmetic Act, Feb. 13, 2024.
Notification of Certification of Invalidity, Unenforceability, and/or Non-Infringement for U.S. Pat. Nos. 11,992,480; 12,005,051; 12,005,052; 12,011,437; And 12,016,848 Pursuant to § 505(j)(2)(B)(iv) of the Federal Food, Drug, and Cosmetic Act, Jul. 16, 2024, 290 pages.
Bethke et al. (2007) "Dose-Proportional Intraindividual Single and Repeated-Dose Pharmacokinetics of Roflumilast, an Oral, Once-Daily Phosphodiesterase 4 Inhibitor" *Journal of Clinical Pharmacology* 47:26-36.
Heo et al. (2010) "Topical effects of roflumilast on 1-chloro-2,4-dinitrobenzene-induced atopic dermatitis-like skin lesions in NC/Nga mice" *Pharmazie* 65:906-12.
Jin et al. (2012) "Phosphodiesterase 4 and Its Inhibitors in Inflammatory Diseases" *Chang Gung Medical Journal* 35(3): 197-210.
Pleasants (2018) "Clinical Pharmacology of Oral Maintenance Therapies for Obstructive Lung Diseases" *Respiratory Care* 63(6):671-89.
Rabe (2011) "Update on roflumilast, a phosphodiesterase 4 inhibitor for the treatment of chronic obstructive pulmonary disease" *British Journal of Pharmacology* 163:53-67.
Notification of Certification of Invalidity, Unenforceability, and/or Non-Infringement for U.S. Pat. No. 12,042,487 Pursuant to § 505(j)(2)(B)(iv) of the Federal Food, Drug, and Cosmetic Act, Sep. 12, 2024, 107 pages.

\* cited by examiner

PHARMACEUTICAL COMPOSITIONS OF ROFLUMILAST AND SOLVENTS CAPABLE OF DISSOLVING HIGH AMOUNTS OF THE DRUG

CROSS REFERENCE TO RELATED APPLICATION

The present application claims priority to U.S. Provisional Application No. 63/406,921, filed on Sep. 15, 2022, the disclosure of which is incorporated herein by reference.

FIELD OF THE INVENTION

The invention relates to topical pharmaceutical compositions comprising roflumilast and solvents that are capable of dissolving surprisingly high amounts of roflumilast. The inventors of the subject application have developed pharmaceutical compositions capable of dissolving surprisingly high amounts of roflumilast relative to other commonly used solvents in approved topical pharmaceutical compositions.

BACKGROUND OF THE INVENTION

Roflumilast is known to be suitable as a bronchial therapeutic agent as well as for the treatment of inflammatory disorders. Compositions containing roflumilast are used in human and veterinary medicine and have been proposed for the treatment and prophylaxis of diseases, including but not limited to: inflammatory and allergen-induced airway disorders (e.g. bronchitis, asthma, COPD); dermatoses (e.g. proliferative, inflammatory and allergen induced skin disorders), and generalized inflammations in the gastrointestinal region (Crohn's disease and ulcerative colitis).

Roflumilast and its synthesis were described in U.S. Pat. No. 5,712,298 (the "'298 patent"), incorporated herein by reference. Although oral tablets of roflumilast have been commercialized, the low aqueous solubility of the compound has been reported to be only 0.53 mg/l at 21° C. in WO95/01338 (corresponding to the '298 patent and incorporated herein by reference). This low aqueous solubility has been problematic for the development of parenteral preparations and topical emulsions, suspensions, gels or solutions containing water. In U.S. Pat. No. 9,205,044 (incorporated herein by reference), the poor water solubility of roflumilast was overcome by using an alkoxylated fat, specifically polyoxyethylated 12-hydroxystearic acid, as a co-solvent for parenteral administration. In EP 1511516B1 (corresponding to U.S. Patent Publication No. 2014/0303215, incorporated herein by reference), the low water solubility of roflumilast was overcome in topical emulsion (cream) formulations by formulating with polyethylene glycol 400 (PEG 400) in concentrations over 62% (w/w) while keeping water weight percentages under 10%.

Topical application for treating skin diseases can provide superior delivery, lower systemic exposure and greater ease of use for patients. The molecular structure of the compound ultimately dictates the ability of the drug to cross the epithelium of the tissue to which the product is applied. For cutaneous application, selection of the components of the formulation dictates the maximum skin permeation that the formulator can achieve.

Several approaches have been proposed for enhancing the solubility of active ingredients with low aqueous solubility. These approaches include particle size reduction, hydrotrophy, precipitation inhibitors (e.g. HPMC, PVP, PVA, PEG) complexation, solvent deposition, alteration of pH, lyophilization, surfactants, co-solvency, microemulsions, solid dispersion and solvate formation.

WO 2013/030789 discloses a PDE-IV inhibitor with poor water solubility in combination with a binder selected from a saccharide (e.g. sucrose, lactose, starches, microcrystalline cellulose, low-viscosity hydroxypropyl cellulose and/or a hydroxypropylmethyl cellulose), protein (e.g. gelatin) or synthetic polymer (e.g. polyethylene glycol, polyvinyl acetate, polyvinyl alcohol and propylene glycol).

In U.S. Pat. No. 9,205,044 (incorporated herein by reference), the poor water solubility of roflumilast was addressed by using alkoxylated fat, specifically polyoxyethylated 12-hydroxystearic acid, as a co-solvent.

In EP 1511516B1, the low water solubility of roflumilast was addressed in topical emulsion formulations (creams) by formulating with polyethylene glycol 400 (PEG 400) in concentrations over 62% (w/w) while keeping water weight percentages under 10%.

U.S. Pat. No. 7,951,398 (incorporated herein by reference) discloses a solid dispersion of roflumilast, which is indicated as a poorly soluble drug, wherein roflumilast is dispersed in a matrix comprising fatty alcohol, triglyceride and fatty acid ester at high temperature, and then cooled and granulated with a hydrophilic polymer.

U.S. Pat. No. 6,074,670 discloses a composition of fenofibrate, which is a poorly soluble drug, which has improved dissolution. The composition includes a hydrophilic polymer and a surfactant, wherein the fenofibrate was granulated with solution of a hydrophilic polymer such as polyvinylpyrrolidone which results in an improved dissolution profile.

U.S. Pat. No. 8,431,154 (incorporated herein by reference) discloses a composition of roflumilast with improved release and an improved pharmacokinetic profile by using an aqueous solution of polyvinylpyrrolidone (PVP) for granulation of roflumilast by preparing a solid solution or solid dispersion.

U.S. Pat. No. 9,340,547 (incorporated herein by reference) discloses that novel PI3K inhibitors can be combined with soluble macromolecular entities, such as cyclodextrin and suitable derivatives thereof or polyethylene glycol-containing polymers in order to improve their solubility, dissolution rate, taste-masking, bioavailability and/or stability.

WO 2015/132708 discloses the use of a multiparticulate composition containing roflumilast and an inert component. The inert component is prepared by granulation and then combined with the roflumilast resulting in a composition with improved dissolution. The composition preferably includes a polyvinyl alcohol as part of the inert component.

One technique for increasing solubility of an active ingredient has been to blend an alcohol or a glycol with water to create a solvent blend that is less polar than water. Because pharmaceutically acceptable alcohols, such as ethanol or isopropyl alcohol, are not desirable excipients for topical application to inflammatory dermatoses due to the tendency to further irritate inflamed skin, propylene glycol is a co-solvent frequently used in topical creams and gels for the treatment of psoriasis or atopic dermatitis. Propylene glycol (abbreviated PG) has been used to increase the solubility of corticosteroids in topical gels, lotions and creams that tend to contain greater than 20% water and volatiles and/or less than 50% hydrocarbons, waxes, or polyols (USP <1151> Definition of Topical Emulsion).

Another solvent that was first used in an FDA-approved topical product in 2005 is diethylene glycol monoethyl ether (Tradename Transcutol®) and abbreviated DEGEE. Diethylene glycol monoethyl ether is used as a vehicle and as a solubilizer for preparing pharmaceutical compositions (for example, see U.S. Pat. No. 9,827,315; U.S. Patent Publication Nos. 2011/0117182 and 2017/0087102, incorporated herein by reference). U.S. Patent Publication No. 2019/009133 describes formulations comprising roflumilast and DEGEE.

SUMMARY OF THE INVENTION

The invention relates to topical pharmaceutical compositions comprising roflumilast and solvents that are capable of dissolving surprisingly high amounts of roflumilast. The inventors of the subject application have developed pharmaceutical compositions capable of dissolving surprisingly high amounts of roflumilast relative to other commonly used solvents in approved topical pharmaceutical compositions. Although some of the solvents disclosed herein have been applied topically in commercially available cosmetic products, many of the solvents disclosed herein have not been used in topical drug products approved for the U.S. market to dissolve high concentrations of active ingredient. The solvents of the present invention are particularly useful when combined with water to maintain high levels of dissolved roflumilast, which is highly insoluble in water.

In certain embodiments, the topical pharmaceutical composition comprises a pharmaceutically effective amount of roflumilast, water, and a solvent selected from the group consisting of 1,3-butylene glycol, 1,2-hexanediol, 1,3-propanediol, 1,2-pentanediol, dipropylene glycol, 2-(2-butoxyethoxy)ethanol, 1,6-hexanediol, propylene glycol methyl ethyl acetate, 5-methyloxolan-2-one, pantolactone, and combinations thereof. In certain embodiments, the pharmaceutically effective amount of roflumilast is an amount of about 0.005% to about 2% w/w. In certain embodiments, the solvent and water are present in an approximately equal molar blend or an approximately 1:2 solvent to water blend (weight:weight). In certain embodiments, the pharmaceutical composition is selected from the group consisting of an emulsion, a gel, and an ointment. In certain embodiments, the pharmaceutical composition further comprises at least one additional component selected from the group consisting of a moisturizer, a surfactant or emulsifier, a polymer or thickener, an antifoaming agent, a preservative, an antioxidant, a sequestering agent, a stabilizer, a buffer, a pH adjusting agent, a skin penetration enhancer, a film former, a dye, a pigment, and a fragrance. In certain embodiments, the solvent is present in an amount sufficient to maintain the stability of the pharmaceutical composition for 1, 2, 3, 6, or 12 months of storage at controlled room temperature and 40° C. In certain embodiments, the solvent is in an amount sufficient to maintain the majority of the roflumilast dissolved after 1, 2, 3, 6, or 12 months of storage at controlled room temperature and 40° C.

In certain embodiments, the topical pharmaceutical composition comprises a pharmaceutically effective amount of roflumilast, 1,3-butylene glycol, and water. In certain embodiments, the pharmaceutically effective amount of roflumilast is an amount of about 0.005% to about 2% w/w. In certain embodiments, the solvent and water are present in an approximately equal molar blend or an approximately 1:2 solvent to water blend (weight:weight). In certain embodiments, the pharmaceutical composition is selected from the group consisting of an emulsion, a gel, and an ointment. In certain embodiments, the pharmaceutical composition further comprises at least one additional component selected from the group consisting of a moisturizer, a surfactant or emulsifier, a polymer or thickener, an antifoaming agent, a preservative, an antioxidant, a sequestering agent, a stabilizer, a buffer, a pH adjusting agent, a skin penetration enhancer, a film former, a dye, a pigment, and a fragrance. In certain embodiments, the solvent is present in an amount sufficient to maintain the stability of the pharmaceutical composition for 1, 2, 3, 6, or 12 months of storage at controlled room temperature and 40° C. In certain embodiments, the solvent is in an amount sufficient to maintain the majority of the roflumilast dissolved after 1, 2, 3, 6, or 12 months of storage at controlled room temperature and 40° C.

In certain embodiments, the topical pharmaceutical composition comprises a pharmaceutically effective amount of roflumilast, 1,2-hexanediol, and water. In certain embodiments, the pharmaceutically effective amount of roflumilast is an amount of about 0.005% to about 2% w/w. In certain embodiments, the solvent and water are present in an approximately equal molar blend or an approximately 1:2 solvent to water blend (weight:weight). In certain embodiments, the pharmaceutical composition is selected from the group consisting of an emulsion, a gel, and an ointment. In certain embodiments, the pharmaceutical composition further comprises at least one additional component selected from the group consisting of a moisturizer, a surfactant or emulsifier, a polymer or thickener, an antifoaming agent, a preservative, an antioxidant, a sequestering agent, a stabilizer, a buffer, a pH adjusting agent, a skin penetration enhancer, a film former, a dye, a pigment, and a fragrance. In certain embodiments, the solvent is present in an amount sufficient to maintain the stability of the pharmaceutical composition for 1, 2, 3, 6, or 12 months of storage at controlled room temperature and 40° C. In certain embodiments, the solvent is in an amount sufficient to maintain the majority of the roflumilast dissolved after 1, 2, 3, 6, or 12 months of storage at controlled room temperature and 40° C.

In certain embodiments, the topical pharmaceutical composition comprises a pharmaceutically effective amount of roflumilast, 1,3-propanediol, and water. In certain embodiments, the pharmaceutically effective amount of roflumilast is an amount of about 0.005% to about 2% w/w. In certain embodiments, the solvent and water are present in an approximately equal molar blend or an approximately 1:2 solvent to water blend (weight:weight). In certain embodiments, the pharmaceutical composition is selected from the group consisting of an emulsion, a gel, and an ointment. In certain embodiments, the pharmaceutical composition further comprises at least one additional component selected from the group consisting of a moisturizer, a surfactant or emulsifier, a polymer or thickener, an antifoaming agent, a preservative, an antioxidant, a sequestering agent, a stabilizer, a buffer, a pH adjusting agent, a skin penetration enhancer, a film former, a dye, a pigment, and a fragrance. In certain embodiments, the solvent is present in an amount sufficient to maintain the stability of the pharmaceutical composition for 1, 2, 3, 6, or 12 months of storage at controlled room temperature and 40° C. In certain embodiments, the solvent is in an amount sufficient to maintain the majority of the roflumilast dissolved after 1, 2, 3, 6, or 12 months of storage at controlled room temperature and 40° C.

In certain embodiments, the topical pharmaceutical composition comprises a pharmaceutically effective amount of roflumilast, 1,2-pentanediol, and water. In certain embodiments, the pharmaceutically effective amount of roflumilast is an amount of about 0.005% to about 2% w/w. In certain embodiments, the solvent and water are present in an approximately equal molar blend or an approximately 1:2 solvent to water blend (weight:weight). In certain embodiments, the pharmaceutical composition is selected from the group consisting of an emulsion, a gel, and an ointment. In certain embodiments, the pharmaceutical composition further comprises at least one additional component selected from the group consisting of a moisturizer, a surfactant or emulsifier, a polymer or thickener, an antifoaming agent, a preservative, an antioxidant, a sequestering agent, a stabilizer, a buffer, a pH adjusting agent, a skin penetration enhancer, a film former, a dye, a pigment, and a fragrance. In certain embodiments, the solvent is present in an amount sufficient to maintain the stability of the pharmaceutical composition for 1, 2, 3, 6, or 12 months of storage at controlled room temperature and 40° C. In certain embodiments, the solvent is in an amount sufficient to maintain the majority of the roflumilast dissolved after 1, 2, 3, 6, or 12 months of storage at controlled room temperature and 40° C.

In certain embodiments, the topical pharmaceutical composition comprises a pharmaceutically effective amount of roflumilast, dipropylene glycol, and water. In certain embodiments, the pharmaceutically effective amount of roflumilast is an amount of about 0.005% to about 2% w/w. In certain embodiments, the solvent and water are present in an approximately equal molar blend or an approximately 1:2 solvent to water blend (weight:weight). In certain embodiments, the pharmaceutical composition is selected from the group consisting of an emulsion, a gel, and an ointment. In certain embodiments, the pharmaceutical composition further comprises at least one additional component selected from the group consisting of a moisturizer, a surfactant or emulsifier, a polymer or thickener, an antifoaming agent, a preservative, an antioxidant, a sequestering agent, a stabilizer, a buffer, a pH adjusting agent, a skin penetration enhancer, a film former, a dye, a pigment, and a fragrance. In certain embodiments, the solvent is present in an amount sufficient to maintain the stability of the pharmaceutical composition for 1, 2, 3, 6, or 12 months of storage at controlled room temperature and 40° C. In certain embodiments, the solvent is in an amount sufficient to maintain the majority of the roflumilast dissolved after 1, 2, 3, 6, or 12 months of storage at controlled room temperature and 40° C.

In certain embodiments, the topical pharmaceutical composition comprises a pharmaceutically effective amount of roflumilast, 2-(2-butoxy-ethoxy)ethanol, and water. In certain embodiments, the pharmaceutically effective amount of roflumilast is an amount of about 0.005% to about 2% w/w. In certain embodiments, the solvent and water are present in an approximately equal molar blend or an approximately 1:2 solvent to water blend (weight:weight). In certain embodiments, the pharmaceutical composition is selected from the group consisting of an emulsion, a gel, and an ointment. In certain embodiments, the pharmaceutical composition further comprises at least one additional component selected from the group consisting of a moisturizer, a surfactant or emulsifier, a polymer or thickener, an antifoaming agent, a preservative, an antioxidant, a sequestering agent, a stabilizer, a buffer, a pH adjusting agent, a skin penetration enhancer, a film former, a dye, a pigment, and a fragrance. In certain embodiments, the solvent is present in an amount sufficient to maintain the stability of the pharmaceutical composition for 1, 2, 3, 6, or 12 months of storage at controlled room temperature and 40° C. In certain embodiments, the solvent is in an amount sufficient to maintain the majority of the roflumilast dissolved after 1, 2, 3, 6, or 12 months of storage at controlled room temperature and 40° C.

In certain embodiments, the topical pharmaceutical composition comprises a pharmaceutically effective amount of roflumilast, 1,6-hexanediol, and water. In certain embodiments, the pharmaceutically effective amount of roflumilast is an amount of about 0.005% to about 2% w/w. In certain embodiments, the solvent and water are present in an approximately equal molar blend or an approximately 1:2 solvent to water blend (weight:weight). In certain embodiments, the pharmaceutical composition is selected from the group consisting of an emulsion, a gel, and an ointment. In certain embodiments, the pharmaceutical composition further comprises at least one additional component selected from the group consisting of a moisturizer, a surfactant or emulsifier, a polymer or thickener, an antifoaming agent, a preservative, an antioxidant, a sequestering agent, a stabilizer, a buffer, a pH adjusting agent, a skin penetration enhancer, a film former, a dye, a pigment, and a fragrance. In certain embodiments, the solvent is present in an amount sufficient to maintain the stability of the pharmaceutical composition for 1, 2, 3, 6, or 12 months of storage at controlled room temperature and 40° C. In certain embodiments, the solvent is in an amount sufficient to maintain the majority of the roflumilast dissolved after 1, 2, 3, 6, or 12 months of storage at controlled room temperature and 40° C.

In certain embodiments, the topical pharmaceutical composition comprises a pharmaceutically effective amount of roflumilast, propylene glycol methyl ethyl acetate, and water. In certain embodiments, the pharmaceutically effective amount of roflumilast is an amount of about 0.005% to about 2% w/w. In certain embodiments, the solvent and water are present in an approximately equal molar blend or an approximately 1:2 solvent to water blend (weight:weight). In certain embodiments, the pharmaceutical composition is selected from the group consisting of an emulsion, a gel, and an ointment. In certain embodiments, the pharmaceutical composition further comprises at least one additional component selected from the group consisting of a moisturizer, a surfactant or emulsifier, a polymer or thickener, an antifoaming agent, a preservative, an antioxidant, a sequestering agent, a stabilizer, a buffer, a pH adjusting agent, a skin penetration enhancer, a film former, a dye, a pigment, and a fragrance. In certain embodiments, the solvent is present in an amount sufficient to maintain the stability of the pharmaceutical composition for 1, 2, 3, 6, or 12 months of storage at controlled room temperature and 40° C. In certain embodiments, the solvent is in an amount sufficient to maintain the majority of the roflumilast dissolved after 1, 2, 3, 6, or 12 months of storage at controlled room temperature and 40° C.

In certain embodiments, the topical pharmaceutical composition comprises a pharmaceutically effective amount of roflumilast, 5-methyloxolan-2-one, and water. In certain embodiments, the pharmaceutically effective amount of roflumilast is an amount of about 0.005% to about 2% w/w. In certain embodiments, the solvent and water are present in an approximately equal molar blend or an approximately 1:2 solvent to water blend (weight:weight). In certain embodiments, the pharmaceutical composition is selected from the group consisting of an emulsion, a gel, and an ointment. In certain embodiments, the pharmaceutical composition further comprises at least one additional component selected from the group consisting of a moisturizer, a surfactant or emulsifier, a polymer or thickener, an antifoaming agent, a preservative, an antioxidant, a sequestering agent, a stabilizer, a buffer, a pH adjusting agent, a skin penetration enhancer, a film former, a dye, a pigment, and a fragrance. In certain embodiments, the solvent is present in an amount sufficient to maintain the stability of the pharmaceutical composition for 1, 2, 3, 6, or 12 months of storage at controlled room temperature and 40° C. In certain embodiments, the solvent is in an amount sufficient to maintain the majority of the roflumilast dissolved after 1, 2, 3, 6, or 12 months of storage at controlled room temperature and 40° C.

In certain embodiments, the topical pharmaceutical composition comprises a pharmaceutically effective amount of roflumilast, pantolactone, and water. In certain embodiments, the pharmaceutically effective amount of roflumilast is an amount of about 0.005% to about 2% w/w. In certain embodiments, the solvent and water are present in an approximately equal molar blend or an approximately 1:2 solvent to water blend (weight:weight). In certain embodiments, the pharmaceutical composition is selected from the group consisting of an emulsion, a gel, and an ointment. In certain embodiments, the pharmaceutical composition further comprises at least one additional component selected from the group consisting of a moisturizer, a surfactant or emulsifier, a polymer or thickener, an antifoaming agent, a preservative, an antioxidant, a sequestering agent, a stabilizer, a buffer, a pH adjusting agent, a skin penetration enhancer, a film former, a dye, a pigment, and a fragrance. In certain embodiments, the solvent is present in an amount sufficient to maintain the stability of the pharmaceutical composition for 1, 2, 3, 6, or 12 months of storage at controlled room temperature and 40° C. In certain embodiments, the solvent is in an amount sufficient to maintain the majority of the roflumilast dissolved after 1, 2, 3, 6, or 12 months of storage at controlled room temperature and 40° C.

DETAILED DESCRIPTION OF THE INVENTION

Before the present invention is described in detail below, it is to be understood that this invention is not limited to the particular methodology, protocols, and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art to which this invention belongs.

All publications, patents and patent applications cited herein are hereby incorporated by reference in their entirety unless otherwise stated. Where the same term is defined in a publication, patent, or patent application and the present disclosure incorporated herein by reference, the definition in the present disclosure represents a controlling definition. For publications, patents and patent applications referenced to describe a particular type of compound, chemistry, etc., the portion relating to such compounds, chemistry, etc. is the portion of the literature incorporated herein by reference.

Note that as used herein, the singular forms "a," "an," and "the" include plural referents unless the context clearly dictates otherwise. Thus, for example, "active ingredient" includes a single ingredient and two or more different ingredients and "solvent" refers to a single solvent and two or more different solvents or a complex mixture of solvents.

The term "about" when used in connection with a numerical value is meant to encompass numerical values within a range having a lower limit that is 5% smaller than the indicated numerical value and having an upper limit that is 5% larger than the indicated numerical value.

The term "effective" refers to an amount of a compound, agent, substance, formulation or composition that is of sufficient quantity to result in a decrease in severity of disease symptoms, an increase in frequency and duration of disease symptom-free periods, or a prevention of impairment or disability due to the disease affliction. The amount may be as a single dose or according to a multiple dose regimen, alone or in combination with other compounds, agents or substances. One of ordinary skill in the art would be able to determine such amounts based on such factors as a subject's size, the severity of a subject's symptoms, and the particular composition or route of administration selected.

"Pharmaceutically acceptable" means generally safe for administration to humans or animals. Preferably, a pharmaceutically acceptable component is one that has been approved by a regulatory agency of the Federal or a state government or listed in the U.S. Pharmacopeia, published by the United States Pharmacopeial Convention, Inc., Rockville Md., or other generally recognized pharmacopeia for use in animals, and more particularly in humans.

A "pharmaceutical composition" according to the invention may be present in the form of a composition, wherein the different active ingredients and diluents and/or carriers are admixed with each other, or may take the form of a combined preparation, where the active ingredients are present in partially or totally distinct form. An example for such a combination or combined preparation is a kit-of-parts.

A "pharmaceutically effective amount" or "therapeutically effective amount" is an amount of a pharmaceutical or therapeutic agent sufficient to achieve the intended purpose. The effective amount of a given therapeutic agent will vary with factors such as the nature of the agent, the route of administration, the size of the subject to receive the therapeutic agent, and the purpose of the administration. The effective amount in each individual case may be determined empirically by a skilled artisan according to established methods in the art.

As used herein, the terms "subject" or "patient" most preferably refers to a human being. The terms "subject" or "patient" may include any mammal that may benefit from the compounds described herein.

The term "substantially" means greater than 90%.

The term "topical" with respect to administration of a drug or composition refers to the application of such drug or composition to the epithelial surface outside the body, including the skin or cornea. For this application, application to the inside of a body opening such as the mouth, nose or ear is not considered a topical application.

As used herein, "treat," "treating," or "treatment" of a disease or disorder means accomplishing one or more of the following: (a) reducing the severity and/or duration of the disorder; (b) limiting or preventing development of symptoms characteristic of the disorder(s) being treated; (c) inhibiting worsening of symptoms characteristic of the disorder(s) being treated; (d) limiting or preventing recurrence of the disorder(s) in patients that have previously had the disorder(s); and (e) limiting or preventing recurrence of symptoms in patients that were previously symptomatic for the disorder(s).

The abbreviation "w/w" represents the relative concentration of the components in the composition as "weight to weight" (i.e., percentage refers to percentage of total weight), rather than based on volume or other quantities.

The invention relates to topical pharmaceutical compositions comprising roflumilast and solvents that are capable of dissolving surprisingly high amounts of roflumilast. The inventors of the subject application have developed pharmaceutical compositions capable of dissolving surprisingly high amounts of roflumilast relative to other commonly used solvents in approved topical pharmaceutical compositions.

The solvents of the present invention are particularly useful when combined with water to maintain high levels of dissolved roflumilast, which is highly insoluble in water.

Roflumilast is a compound of the following formula (I):

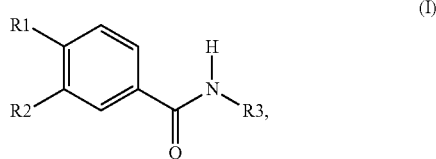

(I)

wherein R1 is difluoromethoxy, R2 is cyclopropylmethoxy and R3 is 3,5-dichloropyrid-4-yl.

This compound has the chemical name N-(3,5-dichloropyrid-4-yl)-3-cyclopropylmethoxy-4-difluoromethoxybenzamide (INN:roflumilast). Roflumilast can be prepared by methods known in the art, for example, as described in the '298 patent and U.S. Patent Publication No. 2014/0303215.

In certain embodiments, the pharmaceutical composition comprises an amount of roflumilast or a salt thereof between about 0.005% to about 2.0% w/w, between about 0.05% to about 1.0% w/w, about 0.05% to about 0.5% w/w, or between about 0.1% to about 0.5% w/w. In certain embodiments, the pharmaceutical composition comprises about 0.005%, 0.01%, 0.02%, 0.03%, 0.04%, 0.05%, 0.06%, 0.07%, 0.08%, 0.09%, 0.10%, 0.15%, 0.20%, 0.25%, 0.30%, 0.35%, 0.40%, 0.45%, 0.50%, 0.55%, 0.60%, 0.65%, 0.70%, 0.75%, 0.80%, 0.85%, 0.90%, 0.95%, 1.0%, 1.1%, 1.2%, 1.3%, 1.4%, 1.5%, 1.6%, 1.7%, 1.8%, 1.9%, or 2.0% w/w of roflumilast or a salt thereof. In certain embodiments, the solvent-water blend can dissolve an amount of about 0.005% up to about 2% of roflumilast. In certain embodiments, the pharmaceutical composition comprises the N-oxide of roflumilast or salts thereof. The amount of the N-oxide of roflumilast or salts thereof can be the same amounts described with respect to roflumilast.

The present invention is directed to pharmaceutical compositions of roflumilast dissolved in one or more solvents and water. In certain embodiments, the solvent is selected from the group consisting of 1,3-butylene glycol, 1,2-hexanediol, 1,3-propanediol, 1,2-pentanediol (also known as pentylene glycol), dipropylene glycol, 2-(2-butoxy-ethoxy) ethanol (also known as butoxydiglycol), 1,6-hexanediol, propylene glycol methyl ethyl acetate (also known as PGMEA or 1-methoxy-2-propanol acetate), 5-methyloxolan-2-one (also known as gamma-valerolactone), pantolactone, 1,3-butanediol, 1,5-pentanediol, 1,6-hexanediol, 1-heptanol, 1-hexanol, 2-(2-ethoxyethoxy)ethyl acetate, 2-(2-methoxyethoxy)ethanol, 2-butoxyethanol, 2-butoxyethyl acetate, 2-ethoxyethanol, 2-ethoxyethyl acetate, 2-methoxyethanol, diethylene glycol dimethyl ether (also known as bis(2-methoxyethyl) ether), diethylene glycol, propylene glycol methyl ether, and combinations thereof. In certain embodiments, the solvent is selected from the group consisting of 1,3-butylene glycol, 1,2-hexanediol, 1,3-propanediol, 1,2-pentanediol, dipropylene glycol, 2-(2-butoxyethoxy)ethanol, 1,6-hexanediol, propylene glycol methyl ethyl acetate, 5-methyloxolan-2-one, pantolactone, and combinations thereof. In certain embodiments, the solvent is selected from the group consisting of 1,2-pentanediol, 5-methyloxolan-2-one, 2-(2-butoxy-ethoxy)ethanol, propylene glycol methyl ethyl acetate, and 1-6-hexanediol.

The pharmaceutical composition preferably contains a solvent in an amount sufficient to obtain the desired level of active ingredient solubility in the formulation. In certain embodiments, the pharmaceutical composition contains an amount of solvent between about 5% and about 50% w/w, between about 10% to about 30% w/w, between about 15% to about 30% w/w, between about 15% to about 25% w/w, between about 20% to about 30% w/w, between about 20% to about 25% w/w, or between about 22.5% and about 27.5% w/w. In certain embodiments, the ratio of solvent to water (weight:weight) is between about 1:50 to about 20:1, between about 1:40 to about 1:1, between about 1:30 to about 1:1, between about 1:20 to about 20:1, or between about 1:20 to about 1:1 weight to weight. The ratio of solvent to water (weight:weight) can be about 1:50, 1:45, 1:40, 1:35, 1:30, 1:25, 1:20, 1:19, 1:18, 1:17, 1:16, 1:15, 1:14, 1:13, 1:12, 1:11, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, or 20:1. In certain embodiments, the ratio of solvent to water (weight:weight) is between about 1:15 to about 1:1 weight to weight, between about 1:14 to about 1:1, between about 1:13 to about 1:1, between about 1:12 to about 1:1, or between about 1:12 to 1:2. In certain embodiments, the ratio of solvent to water is an equal molar blend of solvent to water.

In certain embodiments, the solvent is present in an amount sufficient to maintain the stability of the pharmaceutical composition for 1, 2, 3, 6, or 12 months of storage at controlled room temperature. In certain embodiments, the solvent is capable of maintaining the roflumilast, or at least the majority of the roflumilast, dissolved after 1, 2, 3, 4, 5, 6, or 12 months after storage at controlled room temperature. In certain embodiments, the solvent is capable of maintaining at least 95%, at least 96%, at least 97%, at least 98%, at least 99%, or at least 99.5% of roflumilast dissolved after 1, 2, 3, 4, 5, 6, or 12 months after storage at controlled room temperature.

In certain embodiments, the solvent is present in an amount sufficient to maintain the stability of the pharmaceutical composition for 1, 2, 3, 6, or 12 months of storage at 40° C. In certain embodiments, the solvent is capable of maintaining the roflumilast (or at least substantially all of the roflumilast) dissolved after 1, 2, 3, 4, 5, 6, or 12 months after storage at 40° C. In certain embodiments, the solvent is capable of maintaining at least 95%, at least 96%, at least 97%, at least 98%, at least 99%, or at least 99.5% of roflumilast dissolved after 1, 2, 3, 4, 5, 6, or 12 months after storage at 40° C.

In certain embodiments, the pharmaceutical composition is a topical formulation. The topical roflumilast pharmaceutical formulations can include those defined in U.S. Pharmacopeia USP <1151> and include aerosols, foams, sprays, emulsions (which can also be called creams, lotions, or ointments), gels (two phase or single phase), liquids, ointments, pastes, shampoos, suspensions, and systems. These are typical dosage forms containing pharmaceutically active ingredients for topical application to mammals, including humans.

Topical application refers to dosing the skin, hair, or nails of a patient that will benefit from treatment with a pharmaceutical product. Topical can also mean application to the epithelium of the patient for localized delivery. This would include ophthalmic, otic, oral mucosa, vaginal mucosa, rectal mucosa or urethral application of roflumilast. In certain embodiments, the topical pharmaceutical composition can include using the epithelium of a patient as a route of administration to obtain therapeutic systemic levels of the active ingredient. This form of topical pharmaceutical composition is often referred to as the transdermal delivery of therapeutic active ingredients.

The finished product is preferably in one of the following forms:

An oil-in-water emulsion: The topical product may be an emulsion comprising a discrete hydrophobic phase and a continuous aqueous phase that includes a solvent and water blend and optionally one or more polar hydrophilic excipients as well as salts, surfactants, emulsifiers, and other components. These emulsions may include water-soluble or water-swellable polymers that help to stabilize the emulsion. In certain embodiments, the emulsifier is a self-emulsifying wax blend of dicetyl phosphate and ceteth-10 phosphate.

A water-in-oil emulsion: The compositions may be formulations in which roflumilast is incorporated into an emulsion that includes a continuous hydrophobic phase and an aqueous phase that includes the solvent and optionally one or more polar hydrophilic carrier(s) as well as salts or other components. These emulsions may include oil-soluble or oil-swellable polymers as well as one or more emulsifier(s) that help to stabilize the emulsion. In certain embodiments, the emulsifier is a self-emulsifying wax blend of dicetyl phosphate and ceteth-10 phosphate.

For both oil-in-water and water-in-oil emulsions, the order of addition of the excipients may be important. Roflumilast can be added pre-dissolved in the continuous aqueous phase containing the solvent and water blend. Likewise, roflumilast can be pre-dissolved in the hydrophobic discrete phase of the emulsion that is then mixed with the solvent-water blend and optional hydrophilic excipients that do not contain the active ingredient. Roflumilast can be pre-dissolved in both the oil phase and water phase of the emulsion or added pre-dissolved in the solvent or a solvent-water blend after the emulsion has been formed. Some emulsions undergo phase inversion over a specific temperature range during cooling of the emulsion. Thus, roflumilast may be added to a water-in-oil emulsion above the phase inversion temperature, with the final drug product being an oil-in-water emulsion at controlled room temperature, or vice versa.

Thickened aqueous gels: These systems include a solvent-water blend with dissolved roflumilast and optionally one or more polar hydrophilic carrier(s), such as hexylene glycol which has been thickened by suitable natural, modified natural, or synthetic thickeners as described below. Alternatively, the thickened aqueous gels can be thickened using suitable polyethoxylate alky chain surfactants or other nonionic, cationic, or anionic systems.

Thickened hydroalcoholic gels: These systems include a solvent-water-alcohol blend with dissolved roflumilast and optionally one or more polar hydrophilic carrier(s) such as hexylene glycol as the polar phase which has been thickened by suitable natural, modified natural, or synthetic polymers such as described herein. Alternatively, the thickened hydroalcoholic gels can be thickened using suitable polyethoxylate alky chain surfactants or other nonionic, cationic, or anionic systems. The alcohol can be ethanol, isopropyl alcohol, or another pharmaceutically acceptable alcohol.

A hydrophilic or hydrophobic ointment: The compositions are formulated with a hydrophobic base (e.g. petrolatum, thickened or gelled water insoluble oils, and the like) and optionally have a minor amount of a solvent-water blend with dissolved roflumilast. Hydrophilic ointments generally contain one or more surfactants or wetting agents.

Solvents

In addition to the solvents described above, the compositions may include one or more additional co-solvents to obtain the desired level of active ingredient solubility in the topical product. The co-solvents may also modify skin permeation or the activity of other excipients contained in the formulation. Additional solvents include but are not limited to acetone, ethanol, benzyl alcohol, butyl alcohol, diethyl sebacate, diethylene glycol monoethyl ether (DEGEE), diisopropyl adipate, dimethyl sulfoxide, ethyl acetate, isopropyl alcohol, isopropyl isostearate, isopropyl myristate, N-methyl pyrrolidinone, ethylene glycol, polyethylene glycol, glycerol, propylene glycol, oleic acid, limonene, eugenol, labrosol, and SD alcohol.

Moisturizers

Compositions of the present invention may include a moisturizer to increase the level of hydration. For emulsions, the moisturizer is often a component of the discrete or continuous hydrophobic phase. The moisturizer can be a hydrophilic material including humectants or it can be a hydrophobic material including emollients. Suitable moisturizers include but are not limited to: diethylene glycol monoethyl ether (DEGEE), 1,2,6-hexanetriol, 2-ethyl-1,6-hexanediol, butylene glycol, glycerin, polyethylene glycol 200-8000, butyl stearate, cetostearyl alcohol, cetyl alcohol, cetyl esters wax, cetyl palmitate, cocoa butter, coconut oil, cyclomethicone, dimethicone, docosanol, ethylhexyl hydroxystearate, fatty acids, glyceryl isostearate, glyceryl laurate, glyceryl monostearate, glyceryl oleate, glyceryl palmitate, glycol distearate, glycol stearate, isostearic acid, isostearyl alcohol, lanolin, mineral oil, limonene, medium-chain triglycerides, menthol, myristyl alcohol, octyldodecanol, oleic acid, oleyl alcohol, oleyl oleate, olive oil, paraffin, peanut oil, petrolatum, Plastibase-50W, and stearyl alcohol.

Surfactants and Emulsifiers

Compositions according to the present invention optionally can include one or more surfactants to emulsify the composition and to help wet the surface of the actives or excipients. As used herein the term "surfactant" means an amphiphile (a molecule possessing both polar and nonpolar regions which are covalently bound) capable of reducing the surface tension of water and/or the interfacial tension between water and an immisicible liquid. Surfactants include but are not limited to alkyl aryl sodium sulfonate, Amerchol-CAB, ammonium lauryl sulfate, apricot kernel oil PEG-6 esters, Arlacel, benzalkonium chloride, Ceteareth-6, Ceteareth-12, Ceteareth-15, Ceteareth-30, cetearyl alcohol/ceteareth-20, cetearyl ethylhexanoate, ceteth-10, ceteth-2, ceteth-20, ceteth-23, choleth-24, cocamide ether sulfate, cocamine oxide, coco betaine, coco diethanolamide, coco monoethanolamide, coco-caprylate/caprate, disodium coco-amphodiacetate, disodium laureth sulfosuccinate, disodium lauryl sulfoacetate, disodium lauryl sulfosuccinate, disodium oleamido monoethanolamine sulfosuccinate, docusate sodium, laureth-2, laureth-23, laureth-4, lauric diethanolamide, lecithin, mehoxy PEG-16, methyl gluceth-10, methyl gluceth-20, methyl glucose sesquistearate, oleth-2, oleth-20, PEG 6-32 stearate, PEG-100 stearate, PEG-12 glyceryl laurate, PEG-120 methyl glucose dioleate, PEG-15 cocamine, PEG-150 distearate, PEG-2 stearate, PEG-20 methyl glucose sesqustearate, PEG-22 methyl ether, PEG-25 propylene glycol stearate, PEG-4 dilaurate, PEG-4 laurate, PEG-45/dodecyl glycol copolymer, PEG-5 oleate, PEG-50 Stearate, PEG-54 hydrogenated castor oil, PEG-6 isostearate, PEG-60 hydrogenated castor oil, PEG-7 methyl ether, PEG-75 lanolin, PEG-8 laurate, PEG-8 stearate, Pegoxol 7 stearate, pentaerythritol cocoate, poloxamer 124, poloxamer 181, poloxamer 182, poloxamer 188, poloxamer 237 poloxamer 407, polyglyceryl-3 oleate, polyoxyethylene alcohols, polyoxyethylene fatty acid esters, polyoxyl 20 cetostearyl ether, polyoxyl 40 hydrogenated castor oil, polyoxyl 40 stearate, polyoxyl 6 and polyoxyl 32, polyoxyl glyceryl stearate, polyoxyl stearate, polysorbate 20, polysorbate 40, polysorbate 60, polysorbate 65, polysorbate 80, PPG-26 oleate, PROMULGEN™ 12, propylene glycol diacetate, propylene glycol dicaprylate, propylene glycol monostearate, sodium xylene sulfonate, sorbitan monooleate, sorbitan monopalmitate, sorbitan monostearate, steareth-2, steareth-20, steareth-21, steareth-40, tallow glycerides, and emulsifying wax. In certain embodiments, the emulsifier is a self-emulsifying wax blend of dicetyl phosphate and ceteth-10 phosphate.

Polymers and Thickeners

For certain applications, it may be desirable to formulate a topical product that is thickened with soluble, swellable, or insoluble organic polymeric thickeners such as natural and synthetic polymers or inorganic thickeners including but not limited to acrylates copolymer, carbomer 1382, carbomer copolymer type B, carbomer homopolymer type A, carbomer homopolymer type B, carbomer homopolymer type C, caroboxy vinyl copolymer, carboxymethylcellulose, carboxypolymethylene, carrageenan, guar gum, hydroxyethyl cellulose, hydroxypropyl cellulose, microcrystalline wax, and methylcellulose.

Additional Components

Compositions according to the present invention may be formulated with additional components such as fillers, carriers and excipients conventionally found in cosmetic and pharmaceutical topical products. Additional components including but not limited to antifoaming agents, preservatives (e.g. p-hydroxybenzoic esters, benzyl alcohol, phenylmercury salts, chlorocresol), antioxidants, sequestering agents, stabilizers, buffers, pH adjusting solutions, skin penetration enhancers, film formers, dyes, pigments, diluents, bulking agents, fragrances and other excipients to improve the stability or aesthetics, may be added to the composition.

Compositions according to the present invention may be formulated with additional active agents depending on the condition being treated. The additional active agents include but are not limited to NSAIDs (e.g. Aspirin, Ibuprofen, Ketoprofen, Naproxen), Apremilast, JAK inhibitors (e.g. Tofacitinib, Ruxolitinib, Oclacit), leukotriene inhibitors (e.g. Zileuton, Zafirlukast, Montelukast), mast cell stabilizers (e.g. Nedocromil, Cromolyn sodium, Ketotifen, Pemirolast), Anthralin (dithranol), Azathioprine, Tacrolimus, Coal tar, Methotrexate, Methoxsalen, Salicylic acid, Ammonium lactate, Urea, Hydroxyurea, 5-fluorouracil, Propylthouracil, 6-thioguanine, Sulfasalazine, Mycophenolate mofetil, Fumaric acid esters, Corticosteroids (e.g. Aclometasone, Amcinonide, Betamethasone, Clobetasol, Clocotolone, Mometasone, Triamcinolone, Fluocinolone, Fluocinonide, Flurandrenolide, Diflorasone, Desonide, Desoximetasone, Dexamethasone, Halcinonide, Halobetasol, Hydrocortisone, Methylprednisolone, Prednicarbate, Prednisone), Corticotropin, Vitamin D analogues (e.g. calcipotriene, calcitriol), Acitretin, Tazarotene, Cyclosporine, Resorcinol, Colchicine, bronchodialators (e.g. beta-agonists, anticholinergics, theophylline), and antibiotics (e.g. erythromycin, ciprofloxacin, metronidazole).

Administration and Dosage

The compositions according to the present invention can be administered by any suitable administration route including but not limited to oral, rectal, parenteral (e.g. intradermal, subcutaneous, intramuscular, intravenous, intramedullary, intra arterial, intrathecal, epidural) ocular, inhalation, nebulization, cutaneously (topically), transdermally, and mucosally (e.g. sublingual, buccal, nasally). In a preferred embodiment, the composition is administered topically.

Suitable pharmaceutical dosage forms include but are not limited to emulsions, suspensions, sprays, oils, ointments, fatty ointments, creams, pastes, gels, foams transdermal patches and solutions (e.g. injectable, oral).

The topical formulation containing roflumilast, is applied to the skin in an amount that is sufficient to obtain the desired pharmacologic effect, which typically is to ameliorate the signs and/or symptoms of a medical disorder. The amount of the formulation that is applied may vary depending on the amount of roflumilast that is contained within the formulation, the concentration of the roflumilast within the formulation, and the frequency in which the formulation is intended to be applied. Generally, the formulation is applied with a frequency between weekly to several times daily, preferably between every other day to three times daily, and most preferably one or two times daily.

The composition can be used in veterinary and in human medicine for the treatment and prevention of all diseases regarded as treatable or preventable by using roflumilast, including but not limited to acute and chronic airway disorders such as bronchitis, allergic bronchitis, asthma, and COPD; proliferative, inflammatory and allergic dermatoses such as psoriasis, scalp psoriasis, or inverse psoriasis, irritant and allergic contact eczema, hand eczema, atopic dermatitis, seborrheic dermatitis, lichen simplex, sunburn, aphthous ulcers, lichen planus, vitiligo, pruritus in the genital or anal regions, alopecia areata, hypertrophic scars, discoid lupus erythematosus, follicular and extensive pyodermas, endogenous and exogenous acne, acne rosacea, disorders which are based on an excessive release of TNF and leukotrienes, disorders of the heart which can be treated by PDE inhibitors, inflammations in the gastrointestinal system or central nervous system, disorders of the eye, disorders which can be treated by the tissue-relaxant action of PDE inhibitors and other proliferative, inflammatory and allergic skin disorders; and immune mediated diseases such as arthritis including rheumatoid arthritis, rheumatoid spondylitis, osteoarthritis, and psoriatic arthritis. Preferably, the composition is used to treat proliferative, inflammatory and allergic dermatoses such as psoriasis (vulgaris), eczema, acne, Lichen simplex, sunburn, pruritus, alopecia areata, hypertrophic scars, discoid lupus erythematosus, and pyodermias.

The composition can include additional active agents suitable for treating the patient's condition. For example, when proliferative, inflammatory and allergic dermatoses are treated, the composition may additionally include Anthralin (dithranol), Azathioprine, Tacrolimus, Coal tar, Methotrexate, Methoxsalen, Salicylic acid, Ammonium lactate, Urea, Hydroxyurea, 5-fluorouracil, Propylthouracil, 6-thioguanine, Sulfasalazine, Mycophenolate mofetil, Fumaric acid esters, Corticosteroids (e.g. Aclometasone, Amcinonide, Betamethasone, Clobetasol, Clocotolone, Mometasone, Triamcinolone, Fluocinolone, Fluocinonide, Flurandrenolide, Diflorasone, Desonide, Desoximetasone, Dexamethasone, Halcinonide, Halobetasol, Hydrocortisone, Methylprednisolone, Prednicarbate, Prednisone), Corticotropin, Vitamin D analogues (e.g. calcipotriene, calcitriol), Acitretin, Tazarotene, Cyclosporine, Resorcinol, Colchicine, Adalimumab, Ustekinumab, Infliximab, and/or antibiotics.

The formulation for topical application containing roflumilast, may be prepared by processes typically used in the field of manufacture of pharmaceutical formulations for topical application. In order to make a single-phase formulation, such as a liquid, the constituents of the formulation may be combined and mixed until a homogenous solution or suspension of the active ingredient is obtained. In order to make a multiphase formulation such as an emulsion, for example, the components of the aqueous phase and of the oil phase may be separately combined and mixed until homogenous solutions are obtained and then the aqueous solution and the oil solution may be combined and mixed, such as by shear mixing, to form the formulation. The one or more drug actives may be dissolved (molecularly dispersed), complexed, or associated with an excipient or other active, or may be particulate (amorphous or crystalline). The oil phase may be added to the water phase, or the water phase may be added to the oil phase. The phases may be combined and mixed, such as at elevated temperatures of 50-90° C. or at room temperature, that is between 20-30° C., or at a temperature between room temperature and the elevated temperatures.

EXAMPLES

While various embodiments have been described herein, it should be understood that they have been presented by way of example only, and not limitation. Thus, the breadth and scope of the present disclosure should not be limited by any of the above-described exemplary embodiments. Moreover, any combination of the above-described elements in all possible variations thereof is encompassed by the disclosure unless otherwise indicated herein or otherwise clearly contradicted by context.

Example 1

The solubility of roflumilast in various solvents was determined. Compositions of roflumilast and the solvents identified in Table 1 were prepared. To prepare the compositions, 10 g of a solvent-water blend was added into a 20 mL clear glass vial. 0.05 g of the active pharmaceutical ingredient (API), roflumilast, was added into the vial. The vial was mixed on a jar roller at controlled room temperature at an appropriate speed. A visual evaluation was performed after shaking. If all of the API was dissolved, an additional 0.05 g of API was added into the vial and further mixing was performed. If any API remained undissolved, the total amount of API added to the vial was recorded. The visual inspection was repeated as necessary until no more API could be dissolved. For each solvent, the solubility was determined by syringe filtering (0.2 micron filter) the solvent blend to remove undissolved roflumilast and determining the amount of dissolved roflumilast using HPLC analysis. Composition of the solvent blends were an equal molar solvent-water mixtures, as well as a 1:2 (weight:weight) solvent-water blends. The actual solvent weights used for this study are set forth in Table 1. Transcutol P, which is described for use with roflumilast in U.S. Patent Publication No. 2019/009133, was used as a reference point in Example 1. The solubility results (μg dissolved roflumilast per mL blend) are set forth in Table 1.

TABLE 1

Solvent weights and saturation concentrations (μg/mL) of roflumilast in the solvent blend.

| Solvent (CAS No.) | Equal molar solubility | | | 1:2 solvent to water solubility | | |
|---|---|---|---|---|---|---|
| | grams solvent | grams water | μg roflumilast per mL blend | grams solvent | grams water | μg roflumilast per mL blend |
| 1,3-butylene glycol (107-88-0) | 2.52 | 12.51 | 1.46 | 5.01 | 10.00 | 11.27 |
| 1,2-hexanediol (6920-22-5) | 2.00 | 13.24 | 37.67 | 5.02 | 10.02 | 293.26 |
| 1,3-propanediol (504-63-2) | 3.00 | 12.60 | 2.77 | 5.01 | 10.02 | 6.23 |
| 1,2-pentanediol (3174-67-2) | 2.21 | 12.80 | 4.16 | 5.01 | 10.04 | 139.71 |
| dipropylene glycol (25265-71-8) | 2.02 | 14.84 | 2.27 | 5.01 | 10.01 | 34.44 |
| 2-(2-butoxy-ethoxy)ethanol (112-34-5) | 1.50 | 13.50 | 2.29 | 5.01 | 10.01 | 802.24 |
| 1,6-hexanediol (629-11-8) | 2.00 | 13.11 | 5.81 | 5.01 | 10.02 | 112.31 |
| propylene glycol methyl ethyl acetate (107-98-2) | 2.50 | 12.52 | 6.04 | 5.01 | 10.03 | 65.80 |
| 5-methyl-oxolan-2-one (108-29-2) | 2.51 | 14.03 | 7.80 | 5.01 | 10.01 | 392.14 |
| Pantolactone (599-04-2) | 2.00 | 14.41 | 0.96 | 5.03 | 10.02 | 62.04 |
| Transcutol P (111-90-0) | 2.00 | 14.81 | 2.55 | 5.00 | 10.01 | 45.01 |

As evidenced by the results in Table 1, the studied solvents were capable of dissolving surprisingly high amounts of roflumilast.

Example 2

A topical pharmaceutical composition was prepared as set forth in Table 2.

TABLE 2

Formulation A: Roflumilast 2.0% gel with 2-(2-butoxy-ethoxy)ethanol

| Ingredient | Concentration (% w/w) |
|---|---|
| Roflumilast | 2.00% |
| 2-(2-butoxy-ethoxy)ethanol | 40.00% |
| Benzyl Alcohol | 2.00% |
| Dimethyl Sulfoxide | 20.00% |
| Dimethyl Isosorbide | 10.00% |
| Oleth-2 | 2.00% |
| Propylene Glycol Diacetate | 5.00% |
| Hydroxypropyl Cellulose | 2.00% |
| Purified Water | q.s. ad 100 |

Example 3

A topical pharmaceutical composition was prepared as set forth in Table 3.

TABLE 3

Formulation B: Roflumilast 0.3% cream with 2-(2-butoxy-ethoxy)ethanol

| Ingredient | Concentration (% w/w) |
|---|---|
| Roflumilast | 0.3% |
| 2-(2-butoxy-ethoxy)ethanol | 25.00% |
| White Petrolatum | 10.00% |
| Isopropyl Palmitate | 5.00% |
| Crodafos CES (blend of cetearyl alcohol, dicetyl phosphate, ceteth-10 phosphate) | 10.00% |
| Methylparaben | 0.20% |
| Propylparaben | 0.05% |
| 1N Sodium Chloride | 3.00% |
| Purified Water | q.s. ad 100 |
| 10% w/w Hydrochloric Acid | pH to 5.5 ± 0.4 |
| 1N Sodium Chloride | pH to 5.5 ± 0.4 |

Example 4

A topical pharmaceutical composition was prepared as set forth in Table 4.

TABLE 4

Formulation C: Roflumilast 0.3% cream with propylene glycol methyl ethyl acetate

| Ingredient | Concentration (% w/w) |
|---|---|
| Roflumilast | 0.3% |
| Propylene Glycol Methyl Ether Acetate | 25.00% |
| White Petrolatum | 10.00% |
| Isopropyl Palmitate | 5.00% |
| Crodafos CES (blend of cetearyl alcohol, dicetyl phosphate, ceteth-10 phosphate) | 10.00% |
| Methylparaben | 0.20% |
| Propylparaben | 0.05% |
| 1N Sodium Chloride | 3.00% |
| Purified Water | q.s. ad 100 |
| 10% w/w Hydrochloric Acid | pH to 5.5 ± 0.4 |
| 1N Sodium Chloride | pH to 5.5 ± 0.4 |

Example 5

A topical pharmaceutical composition was prepared as set forth in Table 5.

TABLE 5

Formulation D: Roflumilast 0.1% cream with pentylene glycol (1-2-pentanediol)

| Ingredient | Concentration (% w/w) |
|---|---|
| Roflumilast | 0.1% |
| Pentylene Glycol | 25.00% |
| White Petrolatum | 10.00% |
| Isopropyl Palmitate | 5.00% |
| Crodafos CES (blend of cetearyl alcohol, dicetyl phosphate, ceteth-10 phosphate) | 10.00% |
| Methylparaben | 0.20% |
| Propylparaben | 0.05% |
| 1N Sodium Chloride | 3.00% |
| Purified Water | q.s. ad 100 |
| 10% w/w Hydrochloric Acid | pH to 5.5 ± 0.4 |
| 1N Sodium Chloride | pH to 5.5 ± 0.4 |

Example 6

A topical pharmaceutical composition was prepared as set forth in Table 6.

TABLE 6

Formulation E: Roflumilast 0.3% cream with γ-valerolactone (5-methyloxolan-2-one)

| Ingredient | Concentration (% w/w) |
|---|---|
| Roflumilast | 0.3% |
| γ-valerolactone | 25.00% |
| White Petrolatum | 10.00% |
| Isopropyl Palmitate | 5.00% |
| Crodafos CES (blend of cetearyl alcohol, dicetyl phosphate, ceteth-10 phosphate) | 10.00% |
| Methylparaben | 0.20% |
| Propylparaben | 0.05% |
| 1N Sodium Chloride | 3.00% |
| Purified Water | q.s. ad 100 |
| 10% w/w Hydrochloric Acid | pH to 5.5 ± 0.4 |
| 1N Sodium Chloride | pH to 5.5 ± 0.4 |

Example 7

A topical pharmaceutical composition was prepared as set forth in Table 7.

TABLE 7

Formulation F: Roflumilast 5.0% gel with γ-valerolactone (5-methyloxolan-2-one)

| Ingredient | Concentration (% w/w) |
|---|---|
| Roflumilast | 5.00% |
| γ-valerolactone | 40.00% |
| Benzyl Alcohol | 2.00% |
| Dimethyl Sulfoxide | 20.00% |
| Dimethyl Isosorbide | 10.00% |
| Oleth-2 | 2.00% |
| Propylene Glycol Diacetate | 5.00% |
| Hydroxypropyl Cellulose | 2.00% |
| Purified Water | q.s. ad 100 |

Example 8

A topical pharmaceutical composition was prepared as set forth in Table 8.

TABLE 8

Formulation G: Roflumilast 0.3% w/w cream with 1,6-hexanediol

| Ingredient | Concentration (% w/w) |
|---|---|
| Roflumilast | 0.3% |
| 1,6-hexanediol | 25.00% |
| White Petrolatum | 10.00% |
| Isopropyl Palmitate | 5.00% |
| Crodafos CES (blend of cetearyl alcohol, dicetyl phosphate, ceteth-10 phosphate) | 10.00% |
| Methylparaben | 0.20% |
| Propylparaben | 0.05% |
| 1N Sodium Chloride | 3.00% |
| Purified Water | q.s. ad 100 |
| 10% w/w Hydrochloric Acid | pH to 5.5 ± 0.4 |
| 1N Sodium Chloride | pH to 5.5 ± 0.4 |

Example 9

Two preparations of each of Formulations A, B, C, D, E, F, and G (as set forth in Examples 2-8) were prepared (Prep 1 and Prep 2 in Tables 9-15). Each preparation was stored at controlled room temperature and at 40° C. for three months. The appearance, % w/w, and % LC were assessed after initial preparation (T=0), after one month (T=1), and after three months (T=3).

The assay testing was conducted using an HPLC method. A single-point calibration standard was prepared with a roflumilast concentration of 0.1 mg/mL in acetonitrile. Samples were prepared according to Table 9 below by transferring the specified amount of sample into an appropriate volumetric flask. A syringe was backfilled with sample material to dispense into the flask. The flasks were diluted to approximately half volume with acetonitrile and mixed by vortex for approximately 30 seconds. The flasks were placed into a water bath at 60° C. for 20 minutes. The flasks were then mixed by vortex for approximately 30 seconds. The flasks were allowed to cool to room temperature, diluted to volume with acetonitrile and mixed thoroughly by vortex and inversion. Approximately 1.5 mL of each solution was transferred to Eppendorf microcentrifuge tubes and centrifuged at 16,000 g for 5 minutes. Using a plastic transfer pipette, the supernatant was removed and placed into an autosampler vial. The method was developed using an Agilent 1200 system with a Model G1312B binary high-pressure mixing pump with a dwell volume of about 1.2 mL. The chromatographic parameters are set forth in Table 10 and the gradient is set forth in Table 11. The results of the testing are reported below in Tables 12-18.

TABLE 9

Sample Preparation.

| Roflumilast Formulation Label Claim (% w/w) | Target Weight (mg) | Dilution Volume (mL) |
|---|---|---|
| 0.1 | 670 | 10 |
| 0.3 | 335 | 10 |
| 2 | 250 | 50 |
| 5 | 200 | 100 |

TABLE 10

Chromatographic Parameters.
Chromatographic Parameters

| | |
|---|---|
| Column | Kinetex 5 μm Phenyl-Hexyl 100 Å |
| Mobile Phase A (MPA) | 100% Water |
| Mobile Phase B (MBP) | 100% Acetonitrile |
| Injection Volume | 5 μL |
| Column Temperature | 30° C. |
| Sampler Temperature | Ambient |
| Flow Rate | 1.0 mL/min |
| Detection | 25 nm |
| Spectral Data | 200 to 500 nm (for identification purposes only) |
| Run Time | 38 min |

TABLE 11

Gradient.

| Time (min) | % B |
|---|---|
| 0.00 | 10 |
| 12.85 | 50 |
| 13.00 | 51 |
| 22.15 | 60 |
| 26.65 | 90 |
| 31.65 | 90 |
| 33.00 | 10 |
| 38.00 | 10 |

TABLE 12

Stability Data for Formulation A.

| Testing Parameter | | T = 0 | | Condition | T = 1 | | T = 3 | |
|---|---|---|---|---|---|---|---|---|
| Appearance | | Clear gel | | CRT | Clear gel | | Clear gel | |
| | | | | 40° C. | Clear gel | | Clear gel | |
| | | % w/w | % LC | | % w/w | % LC | % w/w | % LC |
| Assay (% LC) | Prep 1 | 2.008 | 100.4 | CRT | 2.0130 | 100.6 | 2.0382 | 101.9 |
| | | | | 40° C. | 2.0081 | 100.4 | 2.0248 | 101.2 |
| | Prep 2 | 1.992 | 99.6 | CRT | 2.0049 | 100.2 | 1.9820 | 99.1 |
| | | | | 40° C. | 2.0167 | 100.8 | 2.0186 | 100.9 |

TABLE 13

Stability Data for Formulation B.

| Testing Parameter | | T = 0 | | Condition | T = 1 | | T = 3 | |
|---|---|---|---|---|---|---|---|---|
| Appearance | | White cream | | CRT | White cream | | White cream | |
| | | | | 40° C. | Opaque, glossy cream, apparent air migration towards seal | | Opaque, glossy cream, apparent air migration towards seal | |
| | | % w/w | % LC | | % w/w | % LC | % w/w | % LC |
| Assay (% LC) | Prep 1 | 0.3124 | 104.1 | CRT | 0.3070. | 102.3 | 0.3099 | 103.3 |
| | | | | 40° C. | 0.3058 | 101.9 | 0.3128 | 104.3 |
| | Prep 2 | 0.3101 | 103.4 | CRT | 0.3081 | 102.7 | 0.3116 | 103.9 |
| | | | | 40° C. | 0.3112 | 103.7 | 0.3048 | 101.6 |

TABLE 14

Stability Data for Formulation C.

| Testing Parameter | | T = 0 | | Condition | T = 1 | | T = 3 | |
|---|---|---|---|---|---|---|---|---|
| Appearance | | White cream | | CRT | White cream | | White cream | |
| | | | | 40° C. | White cream | | White cream | |
| | | % w/w | % LC | | % w/w | % LC | % w/w | % LC |
| Assay (% LC) | Prep 1 | 0.3160 | 105.3 | CRT | 0.3070 | 102.3 | 0.3164 | 105.5 |
| | | | | 40° C. | 0.3082 | 102.7 | 0.3103 | 103.4 |
| | Prep 2 | 0.3134 | 104.5 | CRT | 0.3088 | 102.9 | 0.3141 | 104.7 |
| | | | | 40° C. | 0.3101 | 103.4 | 0.3126 | 104.2 |

TABLE 15

Stability Data for Formulation D.

| Testing Parameter | | T = 0 | | Condition | T = 1 | | T = 3 | |
|---|---|---|---|---|---|---|---|---|
| Appearance | | White cream | | CRT | White cream Opaque, glossy cream, apparent air migration towards seal | | White cream Opaque, glossy cream, apparent air migration towards seal | |
| | | | | 40° C. | | | | |
| | | % w/w | % LC | | % w/w | % LC | % w/w | % LC |
| Assay (% LC) | Prep 1 | 0.1030 | 103.0 | CRT | 0.1025 | 102.5 | 0.1023 | 102.3 |
| | | | | 40° C. | 0.1031 | 103.1 | 0.1035 | 103.5 |
| | Prep 2 | 0.1032 | 103.2 | CRT | 0.1023 | 102.3 | 0.1029 | 102.9 |
| | | | | 40° C. | 0.1056 | 105.6 | 0.1048 | 104.8 |

TABLE 16

Stability Data for Formulation E.

| Testing Parameter | | T = 0 | | Condition | T = 1 | | T = 3 | |
|---|---|---|---|---|---|---|---|---|
| Appearance | | White cream | | CRT | White cream | | White cream | |
| | | | | 40° C. | White cream | | White cream | |
| | | % w/w | % LC | | % w/w | % LC | % w/w | % LC |
| Assay (% LC) | Prep 1 | 0.2954 | 98.5 | CRT | 0.2982 | 99.4 | 0.3075 | 102.5 |
| | | | | 40° C. | 0.3081 | 102.7 | 0.3075 | 102.5 |
| | Prep 2 | 0.3037 | 101.2 | CRT | 0.3028 | 100.9 | 0.3072 | 102.4 |
| | | | | 40° C. | 0.3020 | 100.7 | 0.3047 | 101.6 |

TABLE 17

Stability Data for Formulation F.

| Testing Parameter | T = 0 | | Condition | T = 1 | | T = 3 | |
|---|---|---|---|---|---|---|---|
| Appearance | Clear gel | | CRT | Clear gel | | Clear gel | |
| | | | 40° C. | Clear gel | | Clear gel | |
| | % w/w | % LC | | % w/w | % LC | % w/w | % LC |
| Assay (% LC) Prep 1 | 4.984 | 99.7 | CRT | 4.9687 | 99.4 | 5.0654 | 101.3 |
| | | | 40° C. | 5.1286 | 102.6 | 5.0578 | 101.2 |
| Prep 2 | 5.086 | 101.7 | CRT | 4.9901 | 99.8 | 5.1020 | 102.0 |
| | | | 40° C. | 5.1196 | 102.4 | 5.0692 | 101.4 |

TABLE 18

Stability Data for Formulation G.

| Testing Parameter | T = 0 | | Condition | T = 1 | | T = 3 | |
|---|---|---|---|---|---|---|---|
| Appearance | White cream | | CRT | White cream | | White cream | |
| | | | 40° C. | White cream | | White cream | |
| | % w/w | % LC | | % w/w | % LC | % w/w | % LC |
| Assay (% LC) Prep 1 | 0.3131 | 104.4 | CRT | 0.3116 | 103.9 | 0.3038 | 101.3 |
| | | | 40° C. | 0.3109 | 103.6 | 0.3129 | 104.3 |
| Prep 2 | 0.3125 | 104.2 | CRT | 0.3156 | 105.2 | 0.3103 | 103.4 |
| | | | 40° C. | 0.3121 | 104.0 | 0.3093 | 103.1 |

The foregoing description has been presented for purposes of illustration and description. This description is not intended to limit the invention to the precise form disclosed. Persons of ordinary skill in the art will appreciate that modifications and substitutions of the basic inventive description may be made.

What is claimed is:

1. A topical pharmaceutical composition comprising a pharmaceutically effective amount of roflumilast, water, and a pharmaceutically acceptable solvent selected from the group consisting of 1,3-butylene glycol, 1,2-hexanediol, 1,3-propanediol, 1,2-pentanediol, dipropylene glycol, 2-(2-butoxy-ethoxy) ethanol, 1,6-hexanediol, propylene glycol methyl ethyl acetate, 5-methyloxolan-2-one, pantolactone, and combinations thereof.

2. The pharmaceutical composition of claim 1, wherein said roflumilast is present in an amount of about 0.005% to about 2% w/w.

3. The pharmaceutical composition of claim 2, wherein the solvent is present in an amount sufficient to maintain the stability of the pharmaceutical composition for 3 months after storage at controlled room temperature.

4. The pharmaceutical composition of claim 2, wherein the solvent is in an amount sufficient to maintain at least 95% of the roflumilast dissolved for 3 months after storage at controlled room temperature.

5. The pharmaceutical composition of claim 2, wherein the solvent is present in an amount sufficient to maintain the stability of the pharmaceutical composition for 3 months after storage at 40° C.

6. The pharmaceutical composition of claim 2, wherein the solvent is in an amount sufficient to maintain at least 95% of the roflumilast dissolved for 3 months after storage at 40° C.

7. The pharmaceutical composition of claim 2, wherein said solvent and water are present in an approximately equal molar blend.

8. The pharmaceutical composition of claim 2, wherein said solvent and water are present in an approximately 1:2 solvent to water blend (weight:weight).

9. The pharmaceutical composition of claim 3, wherein said pharmaceutical composition is selected from the group consisting of an emulsion, a gel, and an ointment.

10. The pharmaceutical composition of claim 9, wherein said pharmaceutical composition further comprises at least one additional component selected from the group consisting of a moisturizer, a surfactant or emulsifier, a polymer or thickener, an antifoaming agent, a preservative, an antioxidant, a sequestering agent, a stabilizer, a buffer, a pH adjusting agent, a skin penetration enhancer, a film former, a dye, a pigment, and a fragrance.

11. The pharmaceutical composition of claim 3, wherein the solvent comprises 1,3-butylene glycol.

12. The pharmaceutical composition of claim 3, wherein the solvent comprises 1,2-hexanediol.

13. The pharmaceutical composition of claim 3, wherein the solvent comprises 1,3-propanediol.

14. The pharmaceutical composition of claim 3, wherein the solvent comprises 1,2-pentanediol.

15. The pharmaceutical composition of claim 3, wherein the solvent comprises dipropylene glycol.

16. The pharmaceutical composition of claim 3, wherein the solvent comprises 2-(2-butoxy-ethoxy) ethanol.

17. The pharmaceutical composition of claim 3, wherein the solvent comprises 1,6-hexanediol.

18. The pharmaceutical composition of claim 3, wherein the solvent comprises propylene glycol methyl ethyl acetate.

19. The pharmaceutical composition of claim 3, wherein the solvent comprises 5-methyloxolan-2-one.

20. The pharmaceutical composition of claim 3, wherein the solvent comprises pantolactone.

* * * * *